United States Patent
Murugesan et al.

(10) Patent No.: US 10,247,675 B2
(45) Date of Patent: *Apr. 2, 2019

(54) MOLECULAR ENHANCED BASED SURFACE ENHANCED RAMAN SPECTROSCOPY TO DETECT LOW CONCENTRATION OF MONOETHANOLAMINE

(71) Applicants: Sankaran Murugesan, Katy, TX (US); Radhika Suresh, Sugar Land, TX (US); Darryl N. Ventura, Houston, TX (US); Bradley G. Harrell, Pearland, TX (US); Valery N. Khabashesku, Houston, TX (US); Qusai A. Darugar, Houston, TX (US)

(72) Inventors: Sankaran Murugesan, Katy, TX (US); Radhika Suresh, Sugar Land, TX (US); Darryl N. Ventura, Houston, TX (US); Bradley G. Harrell, Pearland, TX (US); Valery N. Khabashesku, Houston, TX (US); Qusai A. Darugar, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,506

(22) Filed: May 1, 2018

(65) Prior Publication Data
US 2018/0246039 A1    Aug. 30, 2018

Related U.S. Application Data

(63) Continuation of application No. 15/677,813, filed on Aug. 15, 2017, now Pat. No. 9,958,394, which is a
(Continued)

(51) Int. Cl.
*G01J 3/44* (2006.01)
*G01N 21/65* (2006.01)
(Continued)

(52) U.S. Cl.
CPC ............. *G01N 21/65* (2013.01); *C10G 29/00* (2013.01); *G01N 21/658* (2013.01);
(Continued)

(58) Field of Classification Search
CPC ................. G01N 21/65; G01N 21/658; G01N 2021/656; G01N 33/2835; G01N 21/68; G01J 3/02; G01J 3/44; C10G 29/00
See application file for complete search history.

(56) References Cited

U.S. PATENT DOCUMENTS 9,958,394 B2 * 5/2018 Murugesan ............ G01N 21/65

* cited by examiner

*Primary Examiner* — Abdullahi Nur
(74) *Attorney, Agent, or Firm* — Cantor Colburn LLP

(57) ABSTRACT

A system and method for estimating a concentration of monoethanolamine (MEA) in a fluid. A substrate for supporting a sample of the fluid during testing includes a carbon nanotube mat layer, a silver nanowire layer disposed on the carbon nanotube mat layer, and a chemical enhancer layer disposed on the silver nanowire layer. A sample of the fluid is placed on the substrate, and the fluid sample is radiated with electromagnetic radiation at a selected energy level. A detector measures a Raman spectrum emitted from the sample in response to the electromagnetic radiation. A processor estimates the concentration of MEA in the sample from the Raman spectrum and adds a corrosion inhibitor to the fluid in an amount based on the estimated concentration of MEA to reduce the concentration of MEA in the fluid.

15 Claims, 6 Drawing Sheets

Related U.S. Application Data continuation-in-part of application No. 15/143,886, filed on May 2, 2016.

(51) Int. Cl.
    *G01N 33/28*     (2006.01)
    *C10G 29/00*     (2006.01)
    *G01J 3/02*     (2006.01)

(52) U.S. Cl.
    CPC ... *G01N 33/2835* (2013.01); *C10G 2300/202* (2013.01); *C10G 2300/4075* (2013.01); *G01J 3/02* (2013.01)

MOLECULAR ENHANCED BASED SURFACE ENHANCED RAMAN SPECTROSCOPY TO DETECT LOW CONCENTRATION OF MONOETHANOLAMINE

CROSS REFERENCE TO RELATED APPLICATIONS

The present application is a continuation of U.S. patent application Ser. No. 15/677,813, filed Aug. 5, 2017, issued as U.S. Pat. No. 9,958,394, which is a continuation-in-part of U.S. patent application Ser. No. 15/143,886, filed May 2, 2016, the contents of which are incorporated herein by reference in their entirety.

BACKGROUND

The present disclosure is directed to a method and apparatus for detecting a concentration of chemicals in a process stream in a refinery and, in particular, to using Surface Enhanced Raman Spectroscopy (SERS) to detect concentrations of molecular precursors to corrosive chemicals in hydrocarbon fluids.

Hydrocarbon fluids that are produced from a reservoir include a rich mixture of chemicals, some of which are provided naturally from the formation and some of which end up in the fluid during various stages of petroleum exploration, completion and/or production. Refineries receive feedstocks that include the hydrocarbon fluids and extract or separate out unwanted chemicals. Refinery feedstocks and process streams used in refineries often contain contaminant amines (e.g., from shale oils or upstream $H_2S$ scavenger treatments) which contribute to amine-HCl salt formation in distillation towers and overhead systems of the refinery. Amine-HCl salt corrosion is the most common form of corrosion impacting refinery crude processing units, and monoethanolamine (MEA) is one or the most common and problematic of the contaminant amines. In order to predict corrosion risk or mitigate corrosion cause by a chemical contaminant such as MEA from process streams, it is necessary to detect and determine the concentrations of the chemical in the process stream. Current methods of chemical concentration detection can take from days to weeks to obtain results. A rapid monitoring field method for easily measuring amine levels in process streams is therefore needed to allow an operator to take prompt and appropriate action to mitigate corrosion risk in refinery parts.

BRIEF DESCRIPTION

In one aspect, the present invention provides a method of estimating a concentration of monoethanolamine (MEA) in a fluid, the method including: placing a sample of the fluid on a substrate including: a carbon nanotube mat layer, a silver nanowire layer disposed on the carbon nanotube mat layer, and a chemical enhancer layer disposed on the silver nanowire layer, wherein the fluid sample is placed on the chemical enhancer layer; radiating the fluid sample with electromagnetic radiation at a selected energy level; measuring a Raman spectrum emitted from the fluid sample in response to the electromagnetic radiation; estimating the concentration of MEA in the sample fluid from the Raman spectrum; and adding a corrosion inhibitor to the fluid in an amount based on the estimated concentration of MEA to reduce the concentration of MEA.

In another aspect, the present invention provides a system for estimating a concentration of monoethanolamine (MEA) in a fluid, the system including: a source of electromagnetic radiation for radiating a sample of the fluid at a selected energy level; a substrate for supporting the sample during testing, the substrate including: a carbon nanotube mat layer, a silver nanowire layer disposed on the carbon nanotube mat layer, and a chemical enhancer layer disposed on the silver nanowire layer; a detector configured to measure a Raman spectrum emitted from the sample in response to the electromagnetic radiation; and a processor configured to: estimate the concentration of MEA in the sample from the Raman spectrum, and add a corrosion inhibitor to the fluid in an amount based on the estimated concentration of MEA to reduce the concentration of MEA in the fluid.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
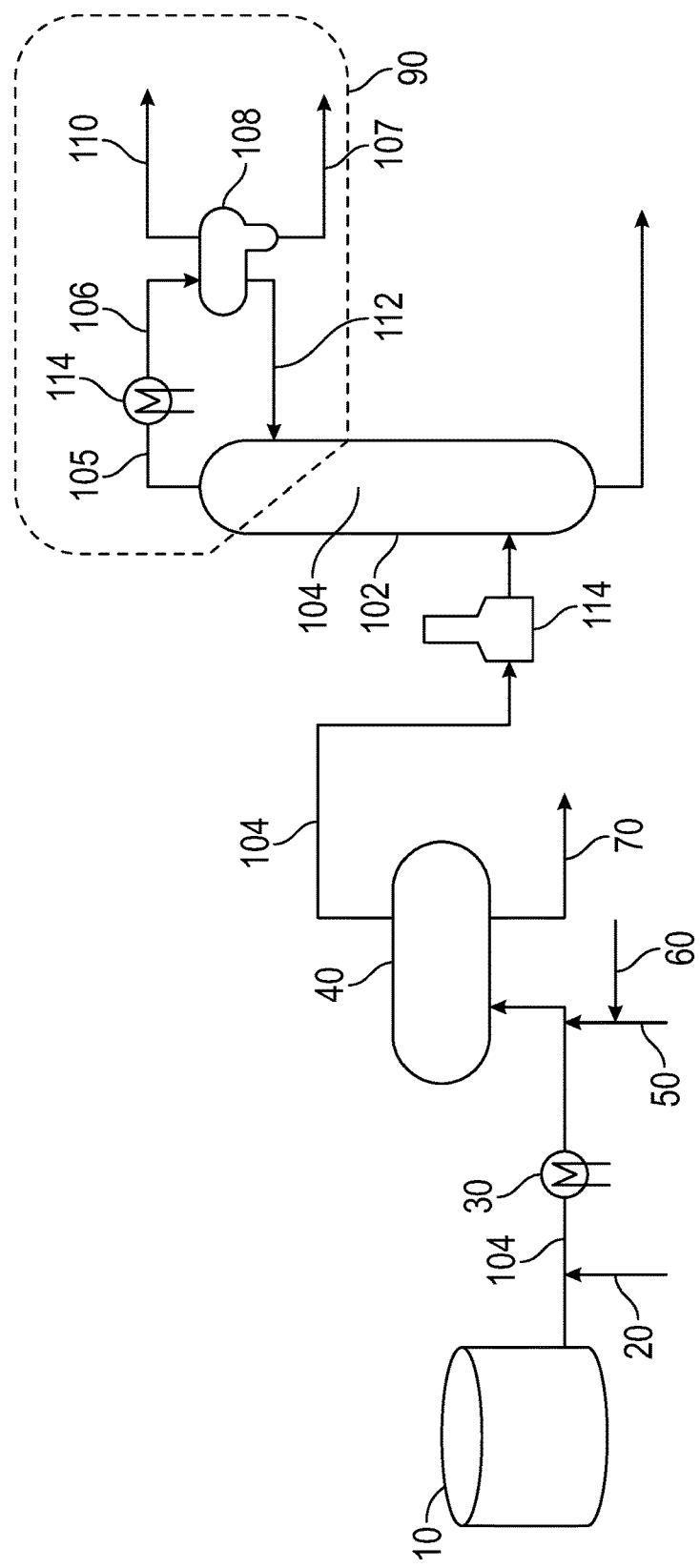
FIG. 1 shows a section of a conduit or fluid passage for flow of fluid according to one embodiment of the present invention.

FIG. 1 shows a refinery 100 to which fluid 104 is generally introduced and can be tested according to one embodiment of the present invention. The refinery section 100 includes overhead distillation tower 102 that separates the fluid components according to their boiling points. The refinery 100 includes a storage tank 10 where crude oil or hydrocarbon fluid 104 can be stored. An injection point 20 provides a location at which caustic or other chloride suppression additive may be injected into the hydrocarbon fluid 104. A heat exchange bank 30 raises the temperature of the hydrocarbon fluid 104. A desalter 40 mixes water with the hydrocarbon fluid 104 and separates the water from the hydrocarbon fluid 104 to removes a salt from the hydrocarbon fluid 104. A desalter water charge 40 is shown upstream of the desalter 40 and provides a desalter wash water. Injection point 60 provides a location at which additive may be injected to react with amines to remove the amines from the hydrocarbon fluid 104. Desalter discharge water 70 or desalter effluent is discharged from the desalter 40 and the fluid 104 proceeds to a furnace heater 114 which heats the hydrocarbon fluid 104 received from the desalter 40 to about +650° F.) and delivers the hydrocarbon fluid to distillation tower 102.

An overhead system 90 is part of a distillation tower 102. Chamber 104 of the distillation tower 102 contains the hydrocarbon fluid 104. A fluid passage 105 from the distillation tower 102 contains mostly gaseous hydrocarbon & water vapor. Heat exchanger 114 condense the hydrocarbon and water. Therefore, fluid passage 106 contains condensed and/or condensing hydrocarbon and water. The hydrocarbon and water in fluid passage 106 is provided to a 3-phase separator 108. Fluid passage 112 exiting the 3-phase separator 108 contains condensed hydrocarbon, which are returned to the distillation tower 102. Fluid passage 110 exiting the 3-phase separator contains light C1-C4 gases, such as low boiling hydrocarbons, H2S, CO2, etc. Fluid passage 107 exiting the 3-phase separator 108 contains a condensed aqueous phase (i.e., overhead water), where most of the amines reside. The fluid passage 107 can be used to provide a fluid sample 120 for SERS testing.

The hydrocarbon fluid 104 is generally fluid that has been extracted from a reservoir in an earth formation. The hydrocarbon fluid 104 may further include an amine such as monoethanolamine (MEA) which is added to the fluid prior to introducing the fluid 104 in the distillation tower 102. MEA may be present as a byproduct from other chemicals added in to the hydrocarbon fluid 104 order to remove hydrogen sulfide ($H_2S$) from the hydrocarbon fluid 104. Hydrogen chloride (HCl) gas may be formed by the decomposition of inorganic compounds during heating of the hydrocarbon fluid. MEA can further react with hydrogen chloride (HCl) that may be present in the hydrocarbon fluid 104 to produce salts that can be corrosive to components of the refinery, such as the distillation tower 102 and overhead system 90, etc. Other amines that may form HCl salts which have a corrosive effect and which can be present in the fluid 104 may include, but are not limited to, ammonia ($NH_3$), dimethylethanolamine (DMEA), methylamine (MA) and methyl diethanolamine (MDEA). Because amine hydrochloride salt formation is a function of amine concentration, HCl concentration, system temperature and system pressure, in order to prevent a selected amine salt from corroding the distillation tower 102 or overhead system 90, a number of strategies may be employed, including injecting additives upstream of the distillation tower 102 to encourage partitioning of the amines from the hydrocarbon phase into an aqueous phase, injection of caustic (or other additive) into the hydrocarbon fluid upstream of the furnace to suppress formation of HCl during heating, or adjusting the operating temperature of the distillation tower 102 such that conditions do not favor formation or deposition of a particular amine salt.

A fluid analyzer 200 (see FIG. 2) is used to determine a concentration of the amine in a fluid sample 120. A fluid passage 107 is as a pipe or conduit that transports the fluid sample 120 from the distillation tower 102 to the fluid analyzer 200. In one aspect, the fluid passage 107 includes the fluid analyzer 200 as an integrated component of the fluid passage 107. Alternatively, the fluid analyzer 200 can be a component connected to a side of the fluid passage 107 and a fluid sample 120 can be diverted from the fluid passage 107 into the fluid analyzer 200. Upon exiting the fluid analyzer 200, the fluid 104 can be delivered to a mixing chamber or returned to distillation tower 102. A strategy for preventing an amine salt from corroding the distillation tower 102, as discussed above, can be employed to provide a suitable amount of additive or corrosion inhibitor 110 into the distillation tower 102 in proportion with the amount of the amine in the fluid sample 120 as determined by the fluid analyzer 200.

Figure 2:
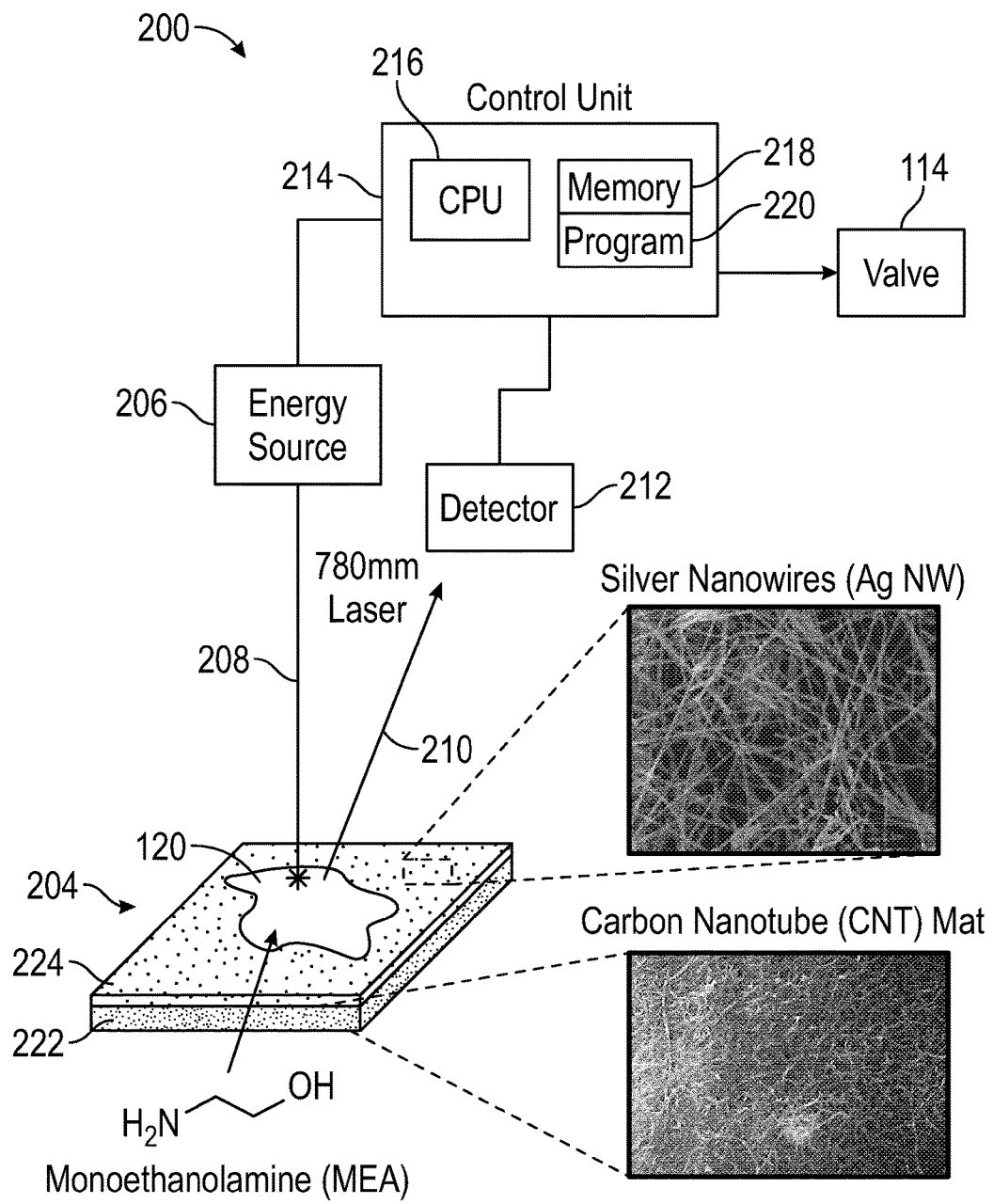
FIG. 2 shows a detailed view of the fluid analyzer of FIG. 1 according to one embodiment of the present invention.

FIG. 2 shows a detailed view of the fluid analyzer 200 of FIG. 1 according to one embodiment of the present invention. The fluid analyzer 200 includes an apparatus for performing Surface Enhanced Raman Spectroscopy (SERS) on a fluid sample 120 drawn from fluid 104 in order to detect trace amounts of a selected chemical in the fluid sample 120. SERS is a surface-sensitive detection technique that is used to detect a composition of analyte adsorbed on rough metal surfaces or nanostructures surfaces. The methods disclosed herein provide enhancements in Raman signals of adsorbed molecules to the order of $10^4$ to $10^6$ which help in detecting analytes at parts per billion (ppb) levels. In the fluid analyzer 200 of the present invention, the fluid sample 120 is deposited on a substrate 204 in a liquid phase and electromagnetic energy 208 is directed at the fluid sample 120 from an energy source 206. In one embodiment, the energy source 206 is a laser and the electromagnetic energy 208 is a monochromatic beam provided at a frequency or energy level that is attuned to at least one of a vibrational or rotational excitation of the selected chemical within the fluid sample 120. The electromagnetic energy 208 excites the electrons of the chemical within the fluid sample 120 to a virtual energy state. As the selected chemical drops back into a lower energy state, it emits photons 210 that can be either lower energy (Stokes scattering) or higher energy (anti-Stokes scattering) than the energy of the incident electromagnetic energy 208. The emitted photons 210 are received at detector 212. The detector 212 generates signals indicative of the energy of the received photon 210 which are sent to control unit 214 for processing.

The control unit 214 includes a processor 216, a memory storage device 218, generally a solid-state memory storage device, and one or more programs 220 stored in the memory storage device 218 and accessible to the processor 216. When the one or more programs 220 are executed or run by the processor 216, the processor 216 produces a spectrum of the emitted photons. The spectrum can be observed or reviewed in order to identify chemicals and relative chemical concentrations within the fluid sample 120. The processor 216 can estimate a concentration level of chemicals with the fluid sample 120 and provide control signals to various components to control a level of the chemicals. Thus the control unit 214 can take an action to control or prevent corrosion at various locations of the refinery 100. While the control unit 214 is described as controlling an addition of an additive to the hydrocarbon fluid 104, in alternate embodiments, an operator can review the detected concentration of the chemical and determine an amount of additive to add to the fluid.

Returning to the substrate 204 of the fluid analyzer 200, the substrate 204 is a composite of conducting carbon materials (such as single-walled carbon nanotubes, double-walled carbon nanotubes, and multi-walled carbon nanotubes), noble metal nanowires, metal oxides and/or other plasmonic metals. The substrate includes a first layer 222 that can include the conductive carbon and a second layer 224 that can include the noble metal nanowires, metal oxides and/or other plasmonic metals. In a particular embodiment, the first layer 222 includes carbon nanotubes (CNTs) and the second layer 224 includes a silver nanowire (Ag NW). The first layer 222 can be formed by filtering CNTs from a suspension. The carbon nanotubes of the first layer 22 can be chemically cross-linked CNTs implemented in the form of flexible carbon nanotube mats, thereby providing a flexible yet durable substrate 204. In various embodiments, the second layer 224 can include metal nanowires, silver nanowires, metal nanowires with metal nanoparticles, and silver nanowires with metal nanoparticles. The metal nanoparticles may be silver nanoparticles and generally have a different aspect ratio than the nanowires of the second layer 224. In an illustrative embodiment, the metal nanowires are silver nanowires. The silver nanowires of the second layer 224 are deposited or formed on top of the first layer 222 in order to coat the first layer 222. The substrate 204 takes advantage of a synergistic SERS effect between the CNTs of the first layer 222 and the silver nanowires of the second layer 224 to enhance the SERS signal. The substrate 204 is stable over a wide range of pH levels and corrosive chemical environments. Due to its flexibility, the substrate 204 can be deformed to fit into a desired shape that suits or conforms to a selected form factor of the fluid analyzer 200. For example, the substrate 204 can be rolled into a scroll, enabling the fluid analyzer to be miniaturized so that it can be implemented as a compact sensor usable to detect chemicals in real-time. The fluid sample 120 is placed on top of the second layer 224 during the testing process. The composition of the CNT-Ag NW substrate 204 enhances the Raman signal of MEA, as discussed below with respect to FIG. 3.

Figure 3:
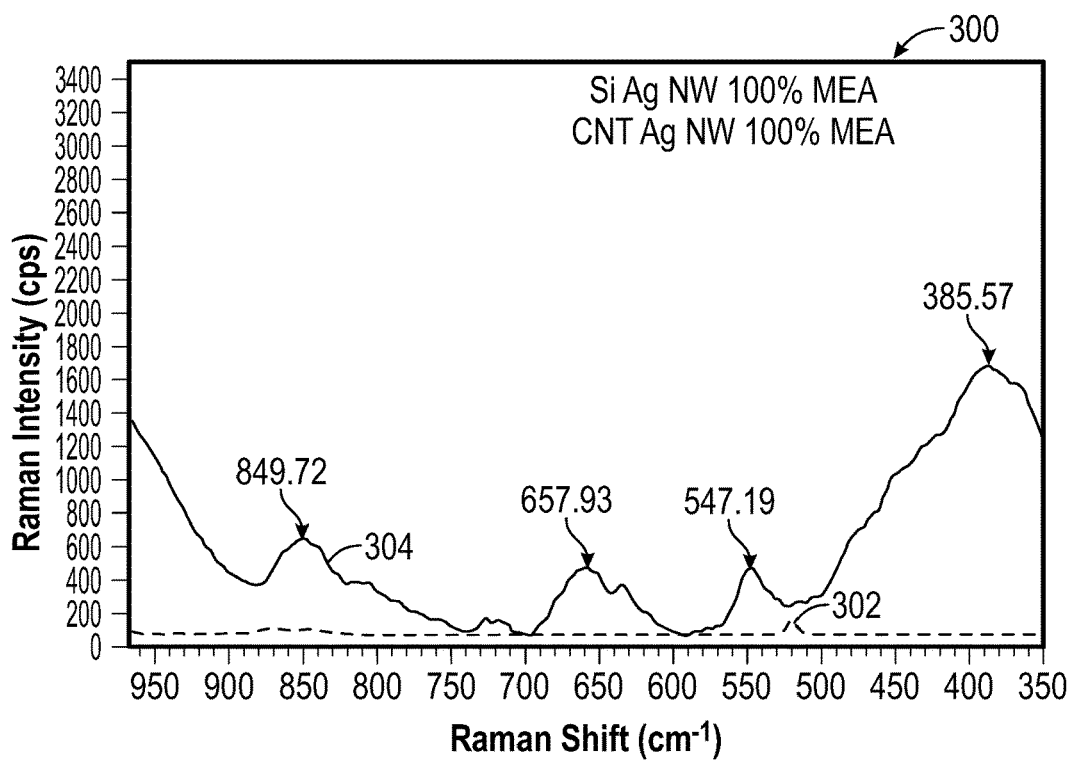
FIG. 3 shows various Raman spectroscopy spectra for a selected chemical obtained by performing SERS on the chemical using different substrates.

FIG. 3 shows various Raman spectroscopy spectra 300 for a selected chemical obtained by performing SERS on the chemical using different substrates. Spectrum 302 represents a spectrum of 100% MEA obtained using SERS with a Silicon Ag NW substrate. Spectrum 304 represents a spectrum of 100% MEA obtained using SERS with a CNT Ag NW substrate. Raman intensity is shown along the ordinate axis and Raman shift is shown along the abscissa. FIG. 3 clearly shows that the peaks of spectrum 304 are more enhanced than the peaks of spectrum 302 and provides a larger signal-to-noise ratio. Using typical Si substrates, the identifying peaks of spectrum 320 have a lower intensity and are often difficult to discern from signal noise. The signal obtained with the CNT Ag NW substrate is approximately 10 times greater than the signal obtained with conventional substrates. Therefore, the CNT Ag NW substrate can be useful in order to identify low concentrations of MEA within the fluid sample 120. In one embodiment, trace amounts of MEA can be detected at concentrations as low as 123 ppm. Such low detection limits enable the sensor technology of the present invention to provide accurate results at field locations, such as in refineries, etc.

Figure 4:
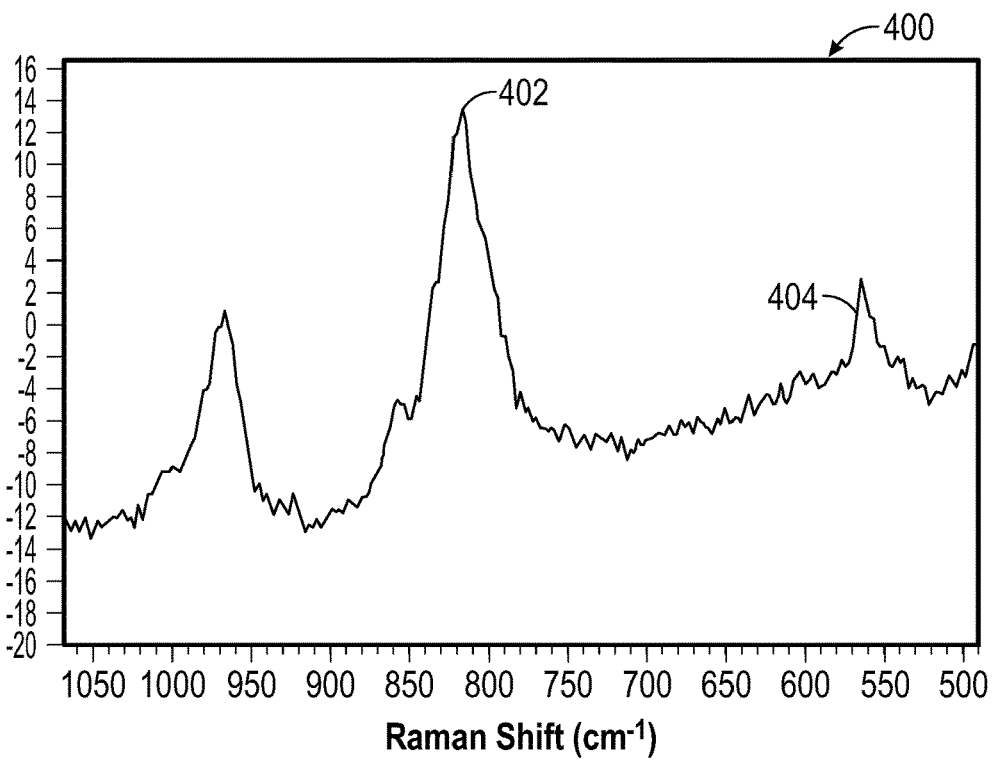
FIG. 4 shows a Raman spectrum for 123 ppm MEA on CNT/Ag NW SERS substrate of FIG. 2.

FIG. 4 shows a Raman spectrum 400 for 123 ppm MEA on CNT/Ag NW SERS substrate of FIG. 2. Raman intensity is shown along the ordinate axis and Raman shift is shown along the abscissa. Peak 402 in the 825 cm$^{-1}$ region and peak 404 in the 550 cm$^{-1}$ region are indicative of the presence of MEA. The spectrum 400 demonstrates that the presence of MEA at about 123 ppm can be reliably detected using the CNT-Ag NW substrate in a SERS testing process.

Figure 5:
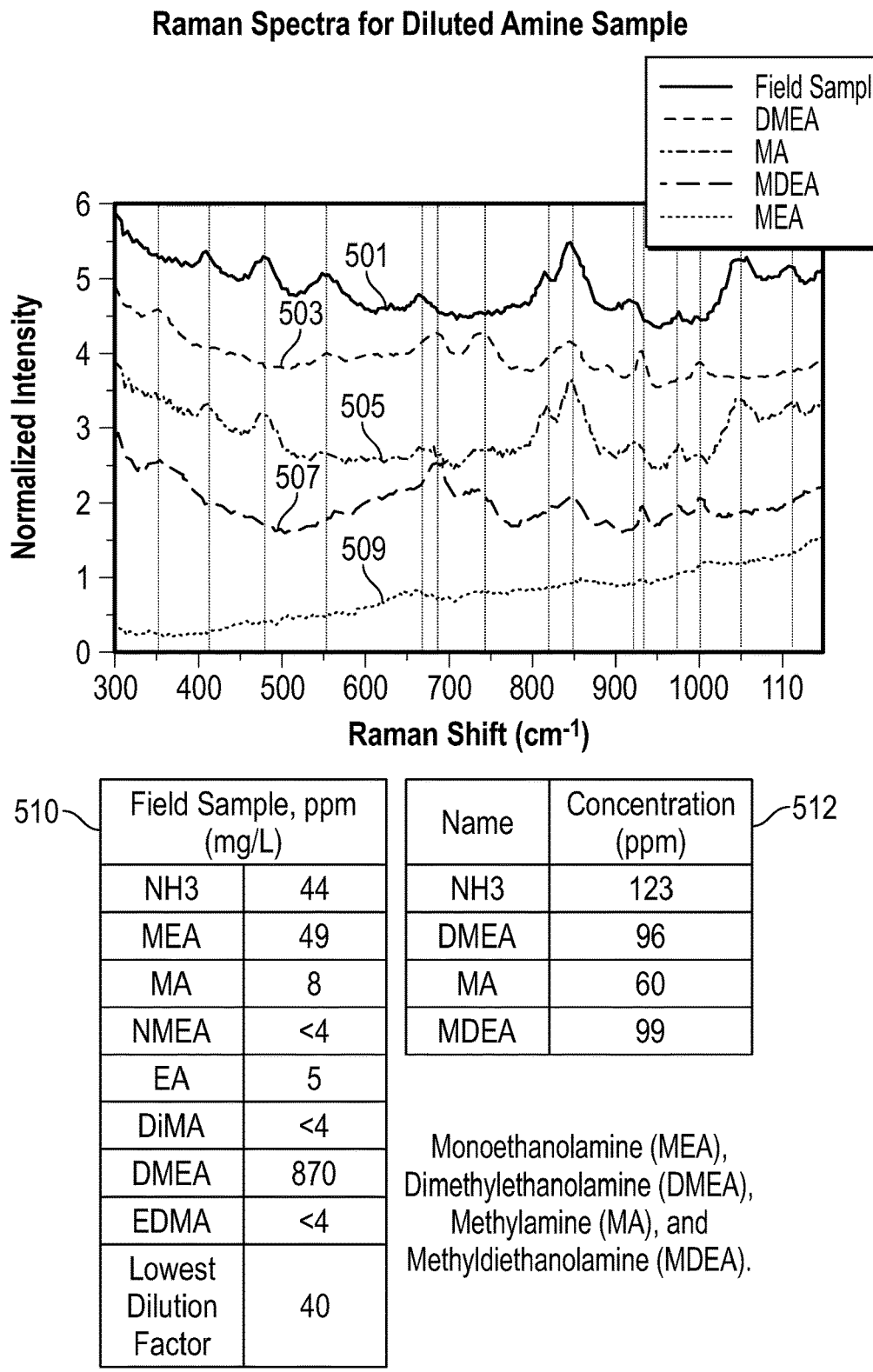
FIG. 5 shows Raman spectra for various diluted amine samples.

The use of the substrate disclosed herein enables selective and quantitative detection amines in addition to MEA. FIG. 5, for example, shows Raman spectra for various diluted amine samples. A spectrum 501 for fluid sample is shown. Spectra 503, 505, 507, 509 indicate the presence of dimethylethanolamine (DMEA), methylamine (MA), methyl diethanolamine (MDEA) and monoethanolamine (MEA), respectively. Concentrations determine using the SERS testing with the substrate disclosed herein are shown in table 510 in milligrams per liter (mg/L) and in table 512 in parts per million (ppm).

While the present invention has been described with respect to refining equipment, the SERS testing process can be performed at refineries, a borehole location, or other suitable location. The sensors disclosed herein can be used to detect the presence of completion fluid in a formation fluid before a well is transitioned into the full production stage. Also, such the methods disclosed herein can be used to detect trace amounts of corrosive of undesired chemicals that are detrimental to downhole equipment or crude oil quality.

Figure 6:
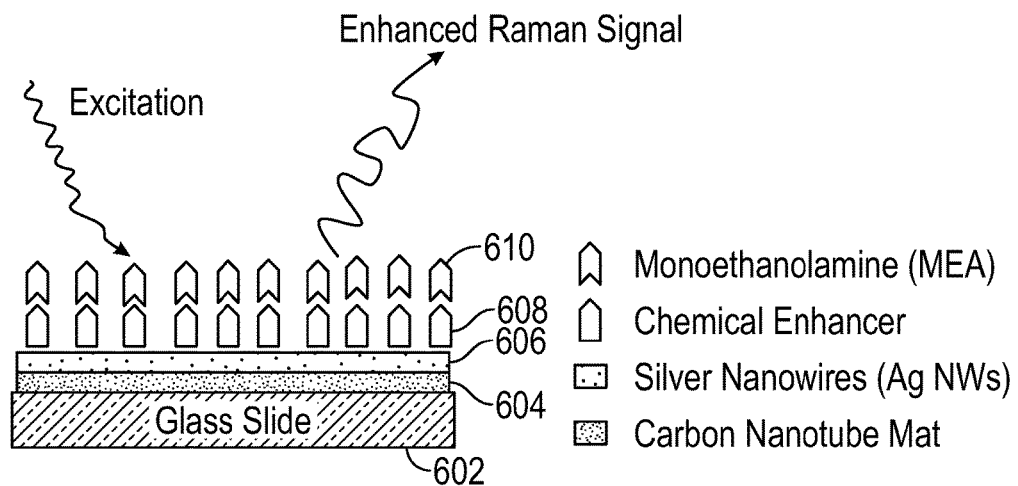
FIG. 6 shows a detailed view of an enhanced SERS substrate suitable for detecting MEA at a concentration level equal to or greater than about 1 ppm.

FIG. 6 shows a detailed view of an enhanced SERS substrate 600 suitable for detecting MEA at a concentration level equal to or greater than about 50 parts per billion (ppb). The enhanced SERS substrate 600 can be used to detect MEA in a fluid sample 120 drawn, for example, from the refinery section 100 of FIG. 1

The enhanced SERS substrate 600 includes a support or base layer 602 for supporting the layers of the enhanced SERS substrate 600. The base layer 602 can be a glass slide, for example. A carbon nanotube mat layer 604 is disposed on the base layer 602. The carbon nanotube mat layer 604 can be a composite of conducting carbon materials (such as single-walled carbon nanotubes, double-walled carbon nanotubes, and multi-walled carbon nanotubes), noble metal nanowires, metal oxides and/or other plasmonic metals. The carbon nanotubes can be interwoven with each other in order to form a flexible mat of carbon nanotubes. In general, the interweaving of the carbon nanotubes is a random interweaving.

A silver nanowire layer 606 is disposed on top of the carbon nanotube layer 604. In a particular embodiment, the silver nanowire layer 606 includes silver nanowires (Ag NW). However, the silver nanowire layer 606 can also include metal nanowires, noble metal nanowires, metal nanowires with metal nanoparticles, silver nanowires with metal nanoparticles, metal oxides and/or other plasmonic metals.

A chemical enhancer layer 608 is formed on the silver nanowire layer 606. The chemical enhancer layer 608 includes a chemical for improving the sensitivity of SERS testing of MEA over a substrate that includes only the carbon nanotube mat layer 604 and the silver nanowire layer 606. SERS testing of MEA using the substrate having only the carbon nanotube mat layer 604 and the silver nanowire layer 606 is able to detect concentrations of MEA equal to or greater than about 10 ppm. By adding the chemical enhancer layer 608, SERS testing is able to detect MEA concentrations equal to or greater than about 50 ppb.

During testing, the fluid sample having MEA 610 is placed on the chemical enhancer layer 608. In various embodiments, the chemical enhancer includes a thiol group for binding to the silver nanowire layer 606 and at least one of a carboxyl group and a boronyl group for bonding to the MEA 610. In one embodiment, the chemical enhancer is 4-mercaptobenzoic acid (4-MBA) But can be at least one of 4-MBA, 2-mercaptopyridine (MPy), 4-bromothiophenol, and 4-nitrothiophenol, in alternate embodiments. In other embodiments, the chemical enhancer can be one of: 4-nitro thiophenol, 4-bromothiophenol, decanethiol, octadecane thiolate, 1,4-benzenedithiol, 4-aminobenzenethiol (4-ATP), 2-naphthalenethiol (2-NT), 4-bromobenzenethiol (4-BBT), 4-chlorobenzenethiol (4-CBT), 4-fluorobenzenethiol (4-FBT), 3,4-dichlorobenzenethiol (3,4-DCT), benzenethiol (BT), 3,5-dichlorobenzenethiol (3,5-DCT), and 2-mercapto-6-methylpyridine (2-MMP), 2-mercaptopyridine (MPy), benzenethiol (BT), mercaptobenzoic acid (MBA), 4-nitrobenzenethiol (4-NBT), 3,4-dicholorobenzenethiol (DBT), 3-fluorothiophenol (3-FTP), 4-fluorothiophenol (4-FTP), and 3,5-bis(trifluoromethyl)benzenethiol (3-FMBT). For boronic compounds, the chemical enhancer can be one of: 4-mercaptophenylboronic acid, 3-thioenyl boronic acid, 4-(Trimethylsilyl)phenylboronic acid, 4-(tert-Butyldimethylsilyloxy)phenylboronic acid, 3-(Methylthio) phenylboronic acid, and 4-(Methylthio)phenylboronic acid.

In other embodiments, the chemical enhancer layer 608 includes a layer of gold particles in which the gold particles are deposited on the silver nanowire layer 608 and the 4-MBA or one of the chemical enhancer listed above is deposited on the gold particles. In another embodiment, the chemical enhancer layer 608 includes only gold nanoparticles.

Figure 7:
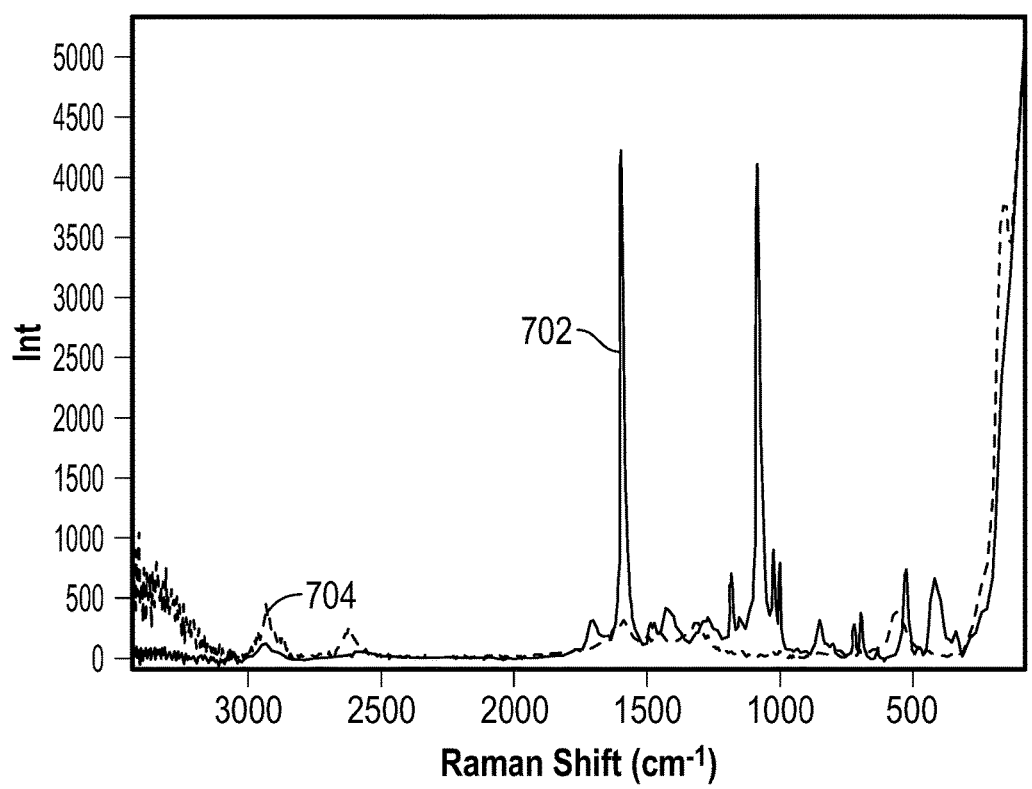
FIG. 7 shows spectra of MEA obtained from SERS testing of a fluid sample having 100 ppm MEA.

FIG. 7 shows spectra of MEA obtained from SERS testing of a fluid sample having 100 ppm MEA. Spectrum 702 shows a Raman spectrum obtained using a substrate having only the carbon nanotube layer 604 and the silver nanowire layer 606. Spectrum 704 shows the Raman spectrum using the enhanced SERS substrate 600 having the additional chemical enhancer layer 608 in which the chemical enhancer is 4-MBA. The signal enhancement of spectrum 702 over spectrum 704 is due to the presence of 4-MBA between the fluid sample and the silver nanowire layer 606.

Figure 8:
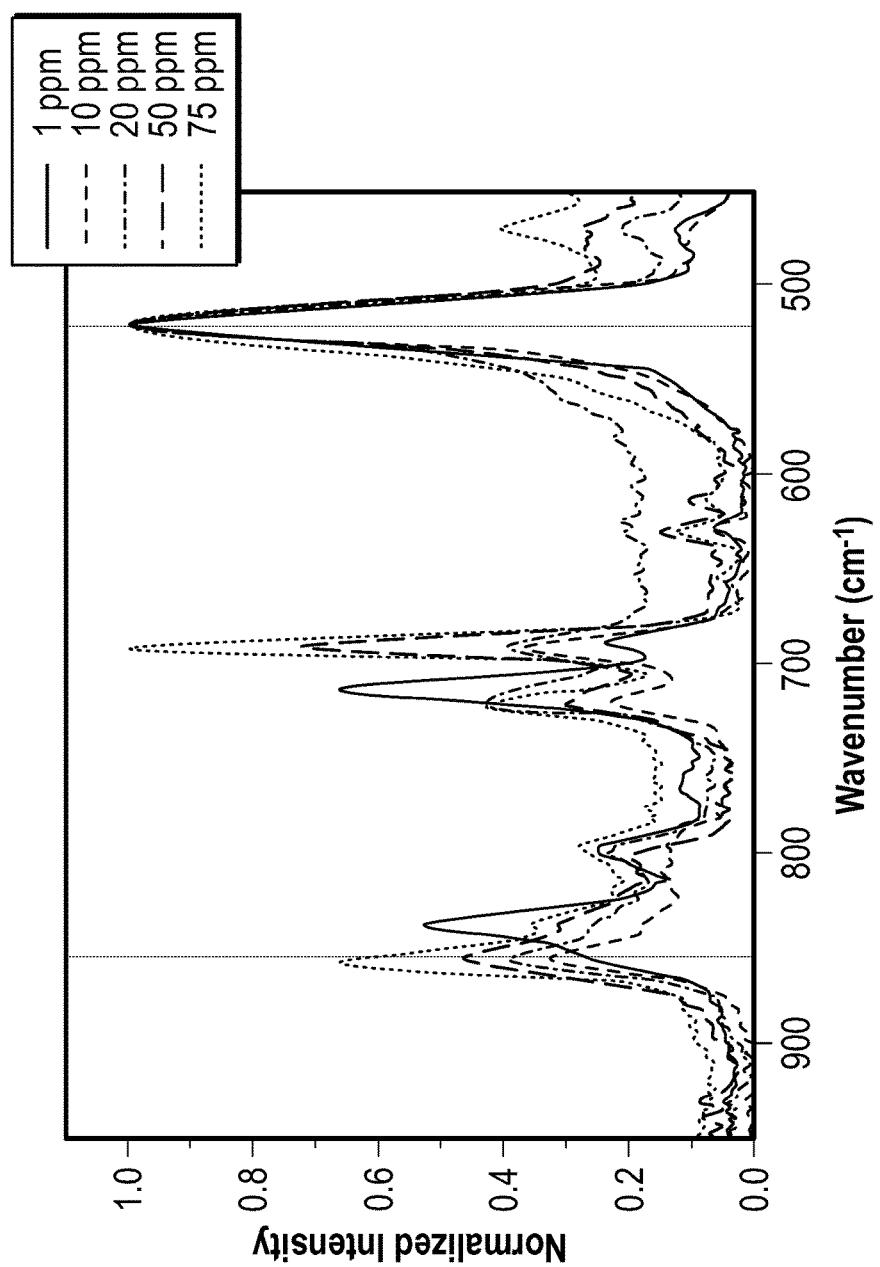
FIG. 8 shows spectra for various concentrations of MEA in a fluid sample as determined using the enhanced SERS substrate of FIG. 6.

FIG. 8 shows spectra for various concentrations of MEA in a fluid sample as determined using the enhanced SERS substrate of FIG. 6. Wave number is shown along the x-axis and normalized intensity is shown along the y-axis. Peaks are shown for MEA concentrations of 75 parts per million (ppm), 50 ppm, 20 ppm, 10 ppm, and 1 ppm. The spectra are normalized to values between 0 and 1 by making the peak value of the spectrum for a 75 ppm fluid sample equal to 1. The peaks in a region about a wave number of about 850 $cm^{-1}$ are selected as reference peaks for the presence of MEA. All of the peaks within this wave number range are detectable based on normalized spectra.

Set forth below are some embodiments of the foregoing disclosure:

Embodiment 1: A method of estimating a concentration of monoethanolamine (MEA) in a fluid, the method including: placing a sample of the fluid on a substrate including: a carbon nanotube mat layer, a silver nanowire layer disposed on the carbon nanotube mat layer, and a chemical enhancer layer disposed on the silver nanowire layer, wherein the fluid sample is placed on the chemical enhancer layer; radiating the fluid sample with electromagnetic radiation at a selected energy level; measuring a Raman spectrum emitted from the fluid sample in response to the electromagnetic radiation; estimating the concentration of MEA in the sample fluid from the Raman spectrum; and adding a corrosion inhibitor to the fluid in an amount based on the estimated concentration of MEA to reduce the concentration of MEA.

Embodiment 2: The method of embodiment 1, wherein the chemical enhancer layer includes a chemical having a thiol group for bonding to the silver nanowire layer and at least one of a carboxyl group and a boronyl group for bonding to the MEA.

Embodiment 3: The method of embodiment 1, wherein the chemical enhancer layer includes at least one of: 4-mercaptobenzoic acid (4-MBA), 2-mercaptopyridine, 4-bromothiophenol, and 4-nitrothiophenol.

Embodiment 4: The method of embodiment 3, wherein the chemical enhancer layer further includes gold nanoparticles, wherein the gold nanoparticles are in contact with the silver nanowires and the at least one of the 4-MBA, 2-mercaptopyridine, 4-bromothiophenol, and 4-nitrothiophenol is disposed on top of the gold nanoparticles.

Embodiment 5: The method of embodiment 1, wherein chemical enhancer layer includes gold nanoparticles.

Embodiment 6: The method of embodiment 1, further comprising determining a presence of MEA at concentration levels equal to or greater than about 50 part per billion.

Embodiment 7: The method of embodiment 1, wherein the fluid is from a refinery, further comprising adding the corrosion inhibitor to the fluid to prevent corrosion in the refinery.

Embodiment 8: A system for estimating a concentration of monoethanolamine (MEA) in a fluid, the system including: a source of electromagnetic radiation for radiating a sample of the fluid at a selected energy level; a substrate for supporting the sample during testing, the substrate including: a carbon nanotube mat layer, a silver nanowire layer disposed on the carbon nanotube mat layer, and a chemical enhancer layer disposed on the silver nanowire layer; a detector configured to measure a Raman spectrum emitted from the sample in response to the electromagnetic radiation; and a processor configured to: estimate the concentration of MEA in the sample from the Raman spectrum, and add a corrosion inhibitor to the fluid in an amount based on the estimated concentration of MEA to reduce the concentration of MEA in the fluid.

Embodiment 9: The system of embodiment 8, wherein the chemical enhancer layer includes a chemical having a thiol group for bonding to the silver nanowire layer and at least one of a carboxyl and a boronyl group for bonding to the MEA Embodiment 10: The system of embodiment 8, wherein the chemical enhancer layer includes at least one of: 4-mercaptobenzoic acid (4-MBA), 2-mercaptopyridine, 4-bromothiophenol, and 4-nitrothiophenol.

Embodiment 11: The system of embodiment 10, wherein the chemical enhancer layer further includes gold nanoparticles, wherein the gold nanoparticles are in contact with the silver nanowires and the at least one of the 4-MBA, 2-mercaptopyridine, 4-bromothiophenol, and 4-nitrothiophenol is disposed on top of the gold nanoparticles.

Embodiment 12: The system of embodiment 8, wherein chemical enhancer layer includes gold nanoparticles.

Embodiment 13: The system of embodiment 8, wherein the chemical enhancer layer enables determining a presence of MEA at concentration levels equal to or greater than about 50 part per billion.

Embodiment 14: The system of embodiment 8, wherein the fluid is from a refinery, further comprising adding the corrosion inhibitor to the fluid to prevent corrosion in the refinery.

Embodiment 15: The system of embodiment 8, wherein the fluid is from one of: (i) a fluid passage at a downstream location of a completion process; (ii) a fluid passage at a downstream location of a crude wash process; and (iii) a fluid passage of an overhead tower of a petroleum refinery.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The teachings of the present disclosure may be used in a variety of well operations. These operations may involve using one or more treatment agents to treat a formation, the fluids resident in a formation, a wellbore, and/or equipment in the wellbore, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A method of estimating a concentration of a selected chemical in a fluid, comprising:
   placing the sample on a substrate comprising:
      a carbon nanotube mat,
      metal nanowires disposed on the carbon nanotube mat, and
      a chemical enhancer disposed on the metal nanowires, wherein the sample is placed in contact with the chemical enhancer;
   radiating the sample with electromagnetic radiation at a selected energy level;
   measuring a Raman spectrum emitted from the sample in response to the electromagnetic radiation;
   estimating the concentration of the selected chemical in the sample from the Raman spectrum; and
   adding a corrosion inhibitor to the sample in an amount based on the estimated concentration of the selected chemical to reduce the concentration of the selected chemical.

2. The method of claim 1, wherein the chemical enhancer includes a chemical having a thiol group for bonding to the metal nanowires and at least one of a carboxyl group and a boronyl group for bonding to the selected chemical.

3. The method of claim 1, wherein the chemical enhancer includes at least one of: 4-mercaptobenzoic acid (4-MBA), 2-mercaptopyridine, 4-bromothiophenol, and 4-nitrothiophenol.

4. The method of claim 3, wherein the chemical enhancer further includes gold nanoparticles, wherein the gold nanoparticles are in contact with the silver nanowires and the at least one of the 4-MBA, 2-mercaptopyridine, 4-bromothiophenol, and 4-nitrothiophenol is disposed on top of the gold nanoparticles.

5. The method of claim 1, wherein chemical enhancer includes gold nanoparticles.

6. The method of claim 1, further comprising determining a presence of the selected chemical at concentration levels equal to or greater than about 50 part per billion.

7. The method of claim 1, wherein the sample is from a refinery, further comprising adding the corrosion inhibitor to the sample to prevent corrosion in the refinery.

8. A system for estimating a concentration of a selected chemical in a sample, comprising:
   a source of electromagnetic radiation for radiating the sample at a selected energy level;
   a substrate for supporting the sample during testing, the substrate comprising:
      a carbon nanotube mat,
      metal nanowires disposed on the carbon nanotube mat, and
      a chemical enhancer disposed on the metal nanowires, wherein the sample is placed in contact with the chemical enhancer;
   a detector configured to measure a Raman spectrum emitted from the sample in response to the electromagnetic radiation; and
   a processor configured to:
      estimate the concentration of the selected chemical in the sample from the Raman spectrum, and
      add a corrosion inhibitor to the sample in an amount based on the estimated concentration of the selected chemical to reduce the concentration of the selected chemical in the sample.

9. The system of claim 8, wherein the chemical enhancer includes a chemical having a thiol group for bonding to the silver nanowire layer and at least one of a carboxyl and a boronyl group for bonding to the selected chemical.

10. The system of claim 8, wherein the chemical enhancer includes at least one of: 4-mercaptobenzoic acid (4-MBA), 2-mercaptopyridine, 4-bromothiophenol, and 4-nitrothiophenol.

11. The system of claim 10, wherein the chemical enhancer further includes gold nanoparticles, wherein the gold nanoparticles are in contact with the silver nanowires and the at least one of the 4-MBA, 2-mercaptopyridine, 4-bromothiophenol, and 4-nitrothiophenol is disposed on top of the gold nanoparticles.

12. The system of claim 8, wherein chemical enhancer includes gold nanoparticles.

13. The system of claim 8, wherein the chemical enhancer enables determining a presence of the selected chemical at concentration levels equal to or greater than about 50 part per billion.

14. The system of claim 8, wherein the sample is from a refinery, further comprising adding the corrosion inhibitor to the sample to prevent corrosion in the refinery.

15. The system of claim 8, wherein the sample is from one of:
   (i) a fluid passage at a downstream location of a completion process; (ii) a fluid passage at a downstream location of a crude wash process; and (iii) a fluid passage of an overhead tower of a petroleum refinery.

* * * * *